United States Patent [19]

Singleton et al.

[11] 4,433,166

[45] Feb. 21, 1984

[54] PROCESS FOR STABILIZING CARBONYLATION CATALYST IN SOLUBLE FORM

[75] Inventors: Thomas C. Singleton, Texas City, Tex.; Frank E. Paulik, St. Louis, Mo.

[73] Assignee: Monsanto Company, St. Louis, Mo.

[21] Appl. No.: 221,231

[22] Filed: Dec. 29, 1980

[51] Int. Cl.$^3$ .................... C07C 51/10; C07C 51/12; C07C 67/36; C07C 67/37
[52] U.S. Cl. .................. 562/519; 260/410.9 R; 260/413; 260/465.4; 560/8; 560/86; 560/97; 560/105; 560/109; 560/114; 560/198; 560/200; 560/204; 560/207; 560/232; 560/233; 560/248; 562/406; 562/497; 562/517; 562/518; 562/520; 562/522; 562/608
[58] Field of Search ............. 562/519, 517, 520, 406, 562/497, 608; 260/413, 410.9 R; 560/232, 204, 97, 8, 105, 109, 114, 198, 200, 86, 248

[56] References Cited

U.S. PATENT DOCUMENTS 3,845,121  10/1974  Eubanks et al. .................. 562/519

FOREIGN PATENT DOCUMENTS 1326014  8/1973  United Kingdom ............... 562/519

*Primary Examiner*—Vivian Garner
*Attorney, Agent, or Firm*—Wendell W. Brooks; Paul L. Passley; Arnold H. Cole

[57] ABSTRACT

The present invention provides for an improved process wherein an olefin, an alcohol, or an ester, halide or ether derivative of said alcohol is reacted with carbon monoxide in a liquid phase in the presence of a catalyst system containing a rhodium component and an iodine or bromine component. By passing at least a portion of the liquid reaction mass from the reaction zone to a separation zone of substantially lower CO partial pressure, at least a portion of the carbonylation products, as well as unreacted carbon monoxide, inert gases, and unreacted olefin, alcohol, or alcohol derivatives are vaporized and can be withdrawn from the separation zone. Precipitation of the rhodium catalyst under carbon monoxide deficient conditions is prevented or retarded by addition to the system of a stabilizer which is a tin component which may be tin or a tin compound.

10 Claims, No Drawings

PROCESS FOR STABILIZING CARBONYLATION CATALYST IN SOLUBLE FORM

BACKGROUND OF THE INVENTION

The present invention relates to a carbonylation process improvement. More particularly, this invention relates to an improved process scheme wherein at least a portion of the reaction mass from a carbonylation process can be withdrawn from the reactor and separated at a lower pressure from a catalyst-containing stream which is recycled to the reactor. In this processing scheme the catalyst is stabilized in soluble form and any of the catalyst which may have precipitated is reconverted to a souble form.

Recently, processes for producing carboxylic acids and esters by carbonylating olefins, alcohols, esters, halides and ethers in the presence of homogeneous catalyst systems that contain rhodium and halogen components such as iodine components and bromine components have been disclosed and placed into commercial operations. These recently developed processes represent a distinct improvement over the classic carbonylation processes wherein such feed materials have been previously carbonylated in the presence of such catalyst systems as phosphoric acid, phosphates, activated carbon, heavy metal salts and metal carbonyls such as cobalt carbonyl, iron carbonyl and nickel carbonyl. All of these previously known processes require the use of extremely high partial pressures of carbon monoxide. These previously known carbonylation systems also have distinct disadvantages in that they require higher catalyst concentrations, longer reaction times, higher temperatures to obtain substantial reaction and conversion rates that all result in larger and more costly processing equipment and higher manufacturing costs.

The discovery that rhodium and iodine or bromine containing catalyst systems will carbonylate such feed materials as olefins, alcohols and esters, halide or ether derivatives of the alcohols at relatively mild pressure and temperature conditions was a distinct contribution to the carbonylation art. In spite of the vast superiority of these newly developed catalyst systems, it has been found that conventional processing schemes for separation of the carbonylation products from the liquid reaction mass has posted problems of catalyst inactivation and precipitation from carbon monoxide-deficient streams.

It has been disclosed in U.S. Pat. No. 3,845,121 that by withdrawing a portion of the liquid reaction mass from the reactor and passing it to a separation zone of substantially lower pressure, without the addition of heat, at least a portion of the carbonylation products can be vaporized and passed on to purification equipment with much reduced decomposition of the carbonylation catalyst system. According to this scheme, the carbonylation reaction is carried out in the reaction zone at a temperature of from about 50° to about 500° C. and a pressure of from about 345 to about 10340 kPa. By withdrawing a portion of the liquid reaction mass and passing it to a separation zone that is maintained at a pressure that is substantially lower than the pressure in the reactor, at least a portion of the carbonylation products will vaporize with much reduced decomposition of the liquid catalyst system. This vaporization will take place without the addition of heat to the reaction mass. The unvaporized liquid in the separation zone containing the catalyst system can be recycled to the reactor.

Using this processing scheme, it has been found that catalyst precipitation may occur, though to a reduced degree, from liquid streams which are deficient in carbon monoxide. Such streams include the stream of reaction mass withdrawn from the reaction zone in which CO has been consumed by reaction and the liquid cycle stream returned from the separation zone to the reaction zone.

From U.S. Pat. No. 3,818,060 it is known that pentavalent nitrogen and phosphorous compounds of the form $XNR_3$ or $XPR_3$ wherein X is oxygen or sulfur may be used as stabilizers for rhodium catalysts in the liquid phase carbonylation of ethylenically unsaturated compounds. Also, from U.S. Pat. No. 3,579,552 it is known that, inter alia, phosphines, amines and trihalostannate compounds form coordination complexes with rhodium and carbon monoxide which remain soluble in the carbonylation of ethylenically unsaturated compounds.

Accordingly, it is an object of this invention to prevent precipitation of the souble catalyst system from CO-deficient streams.

Another object of this invention is to reconvert precipitated components of the catalyst system to soluble form.

Additional objects of this invention will become apparent from the following discussion of the invention.

SUMMARY OF THE INVENTION

The present invention is an improvement in a carbonylation process wherein an olefin, an alcohol, or an ester, halide or ether derivative of said alcohol is reacted with carbon monoxide in a liquid phase in the presence of a catalyst system that contains (a) a rhodium component, and (b) an iodine or bromine component, and in which at least a portion of the carbonylation products are separated from the liquid reaction mass at a reduced CO partial pressure in a separation zone. From this separation zone, an unvaporized liquid stream which is enriched in the catalyst system components is withdrawn and recycled to the reaction zone for reuse in the carbonylation process. A recycle pump is employed to increase the pressure of this liquid stream to enable its transfer back into the higher pressure reaction zone.

Under the conditions of reduced CO partial pressure existing in the separation zone and piping connecting the separation zone to the reaction zone, a small portion of the catalyst system may decompose, forming an insoluble rhodium containing precipitate. According to the present invention, a tin component which may be tin or a tin compound is employed as a catalyst stabilizer for rhodium catalysts in the carbonylation of methanol. Preferably, the tin component is employed in an atomic ratio of at least about 0.5 to the rhodium present.

DESCRIPTION OF THE PREFERRED EMBODIMENTS

This invention is directed to the recently developed carbonylation processes wherein olefins, alcohols and ester, halide and ether derivatives of the alcohols are reacted with carbon monoxide in a liquid phase system in the presence of a homogeneous catalyst system that contains (a) a rhodium, and (b) an iodine or bromine component.

This invention solves the catalyst precipitation problems which may be encountered in the process of separation of the carbonylation products from the liquid mass which involves withdrawing at least a portion of the liquid reaction mass from the reactor and passing it to a separation zone that is maintained at a substantially lower pressure. The lower pressure in the separation zone results in the vaporization at at least a portion of the carbonylation products which are then withdrawn from the separation zone in the vapor form. The unvaporized liquid in the separation zone containing the stable catalyst system can then be recycled to the reactor for reuse in the carbonylation process. According to this invention, the rhodium carbonyl halide catalyst complex is stabilized by addition of a tin component which may be tin or a tin compound. The tin component is employed in an atomic ratio of at least 0.5 of the rhodium present.

When reference is made to the "catalyst system" throughout this disclosure of this invention, it means a catalyst system that forms on combining two distinct components in the presence of carbon monoxide. The two essential catalyst precursor materials are (a) a rhodium, and (b) an iodine or bromine component while CO is a third component.

Rhodium components suitable for use as constituents in the catalyst are described and set out in U.S. Pat. No. 3,845,121, the disclosure of which is incorporated hereby by reference.

The iodine or bromine precursor component of the catalyst system used herein may be in combined from with the rhodium as, for instance, one or more ligands in a coordination compound of the rhodium. However, it is generally preferred to have an excess of the iodine or bromine present in the reaction system over the iodine or bromine that exists as ligands of the rhodium compounds. The bromine or iodine precursor can be in the form of elemental bromine or iodine as well as combinations of bromine or iodine such as hydrogen iodide, hydrogen bromide, alkyl iodide, alkyl bromide, aryl iodide, aryl bromide, iodide salts, bromide salts and the like. Suitable non-limiting examples of such compounds of bromine and iodine include methyl iodide, methyl bromide, ethyl iodide, ethyl bromide, sodium iodide, potassium iodide, sodium bromide, potassium bromide, ammonium iodide, ammonium bromide and the like.

Generally, it is preferred that the amount of iodine precursor material added to the reaction system will be in an amount such that the atomic ratio of the iodine or bromine to the rhodium is above 2:1. Preferably, the atomic ratio of the iodide or bromine to the rhodium will be in a range of 5:1 to 5000:1. A more preferred atomic ratio of the iodine or bromine to the rhodium is 10:1 to 2500:1.

Suitable sources of the tin component include, but are not limited to tin metal, stannous chloride, stannous oxide, organo tin compounds such as tetralkyl tin, stannic chloride, stannic oxide, stannous acetate and the like. The valence of the tin in the tin component may be 0, 2 or 4.

The catalyst system forms by combining the foregoing rhodium and halogen in the presence of carbon monoxide in a liquid reaction medium. The liquid reaction medium employed may include any solvent compatible with the catalyst system and may include pure alcohols or mixtures of the alcohol feedstock and/or the desired carboxylic acid and/or esters of these two compounds. However, the preferred solvent or liquid reaction medium for the process of this invention is the desired carbonylation products such as the carboxylic acid and/or ester of the acid and an alcohol. Water is also often in the reaction mixture to exert a beneficial effect upon the reaction rate.

Suitable feedstock materials for the process are set out in U.S. Pat. No. 3,845,121 previously incorporated by reference.

Methanol and ethylene are two of the most preferred feedstocks that are utilized in the practice of our invention.

In carrying out the carbonylation reaction, the above-mentioned feedstocks are intimately contacted with the above-mentioned catalyst system. The catalyst system can be preformed outside of the reactor by combining the necessary catalyst precursors or it can be formed in situ. Generally, the catalyst will be employed in such amounts as to provide a concentration of soluble rhodium in the reaction medium of from about 10 ppm to about 3000 ppm depending upon the equipment size, desired reaction time and other factors. The carbon monoxide reactant can be sparged into the reactor in such a manner as to intimately contact the carbon monoxide with the reactants in the reaction mass. The presence in the reactor will generally be maintained in the range of from 345 to about 10340 kPa. As disclosed in the prior art, the foregoing known carbonylation process is carried out at a temperature range of from about 50° to about 500° C. with a preferred temperature range of from about 100° to about 250° C. The optimum temperature and pressure maintained in the reactor will vary depending upon the reactants and the particular catalyst system utilized. The catalyst, feedstock materials and general reaction parameters set out in the foregoing discussion are known in the art.

A portion of the liquid phase reaction mass is withdrawn from the reactor and passed to a separation zone that is maintained at a pressure that is lower than the reactor pressure. This pressure reduction will cause at least a portion of the carbonylation products to vaporize and separate from the unvaporized residue of the liquid reaction mass. The aforementioned catalyst system will remain in this residue of unvaporized liquid reaction mass and can be recycled to the reactor.

Generally, it is preferred that the separation zone be maintained at a pressure of at least 138 kPa lower than the pressure in the reactor. The pressure in the reactor is usually in the range of about 345 to 10340 kPa. Thus, the separation zone is maintained at a pressure less than 10200 kPa. It has been found that the separation zone can be maintained at very low pressure, even approaching a complete vacuum; however, it is usually desirable that the separation zone be maintained at a positive pressure to eliminate vapor compression equipment and the like in handling the vaporized carbonylation products that are withdrawn from the separation zone. By maintaining pressure differential of at least 138 kPa between the reactor and the separation zone, a substantial amount of the carbonylation products can be vaporized from the liquid reaction mass.

The exact pressure of the separation zone will vary, depending on the temperature and pressure maintained in the reactor. It is important that the pressure differential between the separation zone and the reactor be at least 138 kPa to insure vaporization of a substantial portion of the carbonylation products in the separation zone. It is also important that the total pressure in the separation zone be less than the vapor pressure of the carbonylation products in the liquid reaction mass withdrawn from the reactor at the temperature of the liquid reaction mass. For example, if at the temperature and pressure of the reactor the carbonylation products to be vaporized have a vapor pressure of 1380 kPa, the separation zone should be operated at a pressure of less than 1240 kPa. Preferably, the separation zone of this invention will be operated at a pressure of from about 69 to 1380 kPa. Most preferably, the separation zone will be operated at a pressure of about 100 to 690 kPa.

The separation zone should be large enough to allow the liquid reaction mass that is passed to it from the reactor to be maintained in said separation zone for a sufficient period of time to vaporize the desired carbonylation products, prior to recycling the unvaporized liquid containing the homogeneous catalyst system back to the reactor. Usually, a residence time of at least one minute in the separation zone is sufficient.

Following separation of the desired carbonylation products, the unvaporized liquid portion of the reaction mass containing any precipitated catalyst decomposition products leaves the separation zone and is introduced into the suction of a recycle pump which increases the pressure of this stream sufficiently to permit its injection back into the reaction zone.

The piping through which a portion of the reaction mass is withdrawn from the reaction zone, as well as the piping through which the liquid recycle stream is transferred back to the reaction zone by the recycle pump, will be at substantially the pressure of the reaction zone. As used herein, "substantially the pressure of the reaction zone" means the reaction zone pressure plus or minus pressure changes caused by fluid flow through the respective lines.

Depending upon the temperature and pressure of the transfer piping, a minor amount of the carbonylation catalyst system according to the prior art (i.e., not including the tin stabilizer component of the present invention) may decompose and precipitate from the liquid in the piping. The catalyst system is believed to comprise a carbonyl complex of the rhodium component and the halide component, and it is further believed that carbon monoxide may be abstracted from a portion of the carbonyl complex form of the catalyst system, converting some of the catalyst to an insoluble form which may comprise a rhodium halide. Because the rhodium component of the catalyst system is quite expensive, it is desirable to recover any traces of precipitated catalyst for return to the reaction zone and reuse.

According to the present invention, the rhodium catalyst is maintained in soluble form in these carbon monoxide deficient portions of the process by addition to the system of a tin component which may be tin or a tin compound.

The tin stabilizer component is employed in an atomic ratio of at least about 0.5 to the rhodium present in the catalyst system. The tin stabilizer component may be injected into the carbonylation reaction system at any convenient point, but is preferably injected into the transfer piping leading from the carbonylation reactor to the separation zone, or into the piping which conducts the catalyst-containing recycle stream from the separation zone back to the reactor, in order to insure complete mixing of the tin component with the catalyst-containing liquid system.

The practice of this invention is illustrated by the following examples which should not be construed as limiting the invention in any way.

In the following examples a stock solution was prepared which simulated the liquid recycle stream which is returned from the separation zone to the carbonylation reactor in a typical acetic acid plant. Included in this solution were traces of iron, nickel, chromium and molybdenum normally found in acetic acid plants as corrosion products. The stock solution employed acetic acid as the solvent and contained the following:

| | |
|---|---|
| Iron | 0.025 moles/liter |
| Nickel | 0.02 moles/liter |
| Chromium | 0.016 moles/liter |
| Molybdenum | 0.01 moles/liter |
| Water | 9.5 moles/liter |
| Total iodides | 0.5 moles/liter |
| Labile methyl groups (methyl iodide + methanol + methyl acetate) | 0.35 moles/liter |

EXAMPLE 1

To establish a base run in which no tin component stabilizer was present, the following experiment was performed. About 650 milliliters of the stock solution described above plus a rhodium solution and hydrogen iodide was charged into a 1500 milliliter stirred autoclave and pressured with carbon monoxide to a pressure of 791 kPa. The contents were heated with stirring and when a temperature of 150°–155° C. was reached methanol and methyl iodide were added. The autoclave contents were then immediately cooled to 125°–128° C. under a pressure of 205 kPa, refluxed, and were sampled and found to contain 444 parts per million (ppm) dissolved rhodium.

The autoclave contents were sampled periodically and anlyzed for dissolved rhodium. The results of these analyses were as follows:

| Time After Methanol Addition (minutes) | ppm Dissolved Rhodium | % of Original Dissolved Rhodium |
|---|---|---|
| 63 | 249 | 56 |
| 93 | 166 | 37 |
| 153 | 79 | 18 |

This experiment clearly demonstrates that in the absence of a catalyst stabilizer the rhodium rapidly precipitates from the solution in the autoclave.

EXAMPLE 2

Using the equipment and procedure of Example 1, the base case run was repeated except that the autoclave solution contained 0.00512 mols/liter of anhydrous $SnCl_4$. Total iodine and total labile methyl groups were as in Example 1 initially. Initial dissolved rhodium was 434 ppm. Samples were taken and analyzed periodically while the temperature was maintained at 125°–126° C. and the following results obtained:

| Time After Methanol Addition (minutes) | ppm Dissolved Rhodium | % of Original Dissolved Rhodium |
|---|---|---|
| 62 | 462 | 106 |
| 128 | 462 | 106 |

These results clearly indicate that the tin stabilizer greatly retarded the rate of rhodium precipitation from the autoclave solution.

EXAMPLES 3-7

To show the variety of tin components which may be used as stabilizers, the experiment of Example 1 was repeated except that the autoclave solution contained the tin components shown in the following Table as a stabilizer. The initial total iodine level and the initial total labile methyl groups were as in Example 1 and the initial dissolved rhodium was as shown in the Table. Periodic samples for dissolved rhodium gave the results shown. In all cases, the tin component was present in a concentration of 0.0045 moles/liter, except in Example 3 the tin component concentration was 0.0046 moles/liter.

TABLE

| Example | Tin Component | Temperature (°C.) | Time (minutes) | Dissolved Rhodium (ppm) | % of Original Dissolved Rh |
|---|---|---|---|---|---|
| 3 | SnO | 127-130 | Initial | 425 | 100 |
|   |     |         | 60      | 449 | 106 |
|   |     |         | 120     | 448 | 105 |
| 4 | $K_2SnO_3$ | 128-129 | Initial | 425 | 100 |
|   |     |         | 65      | 422 | 99  |
|   |     |         | 125     | 433 | 103 |
| 5 | Stannous Linoleate | 128-129 | Initial | 444 | 100 |
|   |     |         | 63      | 452 | 102 |
|   |     |         | 133     | 434 | 98  |
| 6 | Dibutyl tin-bis(2-ethyl hexanoate) | 127-129 | Initial | 435 | 100 |
|   |     |         | 65      | 404 | 93  |
|   |     |         | 125     | 287 | 66  |
| 7 | Tetrabutyl tin | 128-131 | Initial | 435 | 100 |
|   |     |         | 64      | 319 | 73  |
|   |     |         | 124     | 136 | 31  |

What is claimed is:

1. In a carbonylation process wherein at least one reactant selected from the group consisting of an alcohol, an ester derivative of said alcohol, a halide derivative of said alcohol and an ether derivative of said alcohol is (1) reacted with carbon monoxide in a liquid phase in a reaction zone and in the presence of a catalyst system that contains (a) a rhodium component, and (b) an iodine or bromine component, (2) passing at least a portion of the liquid reaction mass in which the carbon monoxide has been depleted from the reaction zone to a separation zone, and (3) recycling the remaining liquid reaction mass from the separation zone to said reaction zone, the improvement which comprises adding to the process an amount of a tin component which may be tin or a tin compound, said amount being sufficient to maintain the rhodium component in soluble form.

2. The process of claim 1 wherein the catalyst system contains a rhodium component and an iodine component.

3. The process of claim 2 wherein methanol is carbonylated to acetic acid.

4. The process of claim 3 wherein said acid is present in a molar ratio of at least about 0.5 to the rhodium component.

5. The process of claim 4 wherein the tin component is tin metal.

6. The process of claim 4 wherein the tin component is $SnCl_4$.

7. The process of claim 4 wherein the tin component is SnO.

8. The process of claim 4 wherein the tin component is $K_2SnO_3$.

9. The process of claim 4 wherein the tin component is stannous acetate.

10. The process of claim 4 wherein the tin component is stannous linoleate.

* * * * *